US00PP32817P2

(12) United States Plant Patent
Robacker et al.

(10) Patent No.: US PP32,817 P2
(45) Date of Patent: Feb. 16, 2021

(54) ***ABELIA* PLANT NAMED '00-BC-46-4'**

(50) Latin Name: ***Abelia* hybrid**
Varietal Denomination: 00-BC-46-4

(71) Applicant: University of Georgia Research Foundation, Inc., Athens, GA (US)

(72) Inventors: Carol Robacker, Peachtree City, GA (US); Sloane Michele Scheiber, Parkesburg, PA (US); Sherrod Baden, Milner, GA (US); Allen Byous, Thomaston, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 16/873,532

(22) Filed: Apr. 30, 2020

(51) Int. Cl.
*A01H 5/02* (2018.01)

(52) U.S. Cl.
USPC ..... Plt./226

(58) Field of Classification Search
USPC ..... Plt./226
See application file for complete search history.

*Primary Examiner* — Annette H Para
(74) *Attorney, Agent, or Firm* — Thomas | Horstemeyer, LLP

(57) ABSTRACT

A new and distinct cultivar of *Abelia* plant named '00-BC-46-4', characterized by a combination of attractive foliage, compact form, large flower panicles, heavy blooming, and low maintenance requirements.

2 Drawing Sheets

Botanical designation: *Abelia* hybrid.
Cultivar denomination '00-BC-46-4.'.

BACKGROUND OF THE INVENTION

The present invention relates to a new and distinct cultivar of the ornamental flowering shrub *Abelia* hereinafter referred to by the varietal denomination '00-BC-46-4'.

The new *Abelia* '00-BC-46-4' is a product of a planned breeding program conducted by the inventors in Griffin, Ga. The objective of the *Abelia* breeding program is to produce a tough and adaptable drought-tolerant plant with commercial value. This cultivar has significant commercial and home gardener appeal with its attractive foliage, large flower panicles, heavy blooming and low maintenance requirements. These and other qualities are enumerated herein.

Pedigree and History: The new *Abelia* '00-BC-46-4' originated from a cross in 1998 between *Abelia chinensis* R. Br. (unpatented, female parent) and *Abelia* x *grandiflora* (Andr) Rehd 'Francis Mason' (unpatented, male parent). A seedling selection from this cross, 99-54-3, was backcrossed to the original *A. chinensis* parent in 2000, and ovule culture was performed to obtain seedlings. In September 2001, these seedlings were planted in a field plot in Griffin, Ga. (USDA cold hardiness zone 8a). Selection criteria included flowering and foliage characteristics, plant form and height, cold hardiness and drought tolerance. Plant '00-BC-46-4' was selected for further evaluation and was asexually propagated via shoot cuttings for evaluation in a field plot in Griffin, Ga. in 2004 and in 2006 (6 reps each time, randomized block design), in Blairsville, Ga. (USDA cold hardiness zone 7a) in 2005 (4 reps, randomized block design), and in containers at the Center for Applied Nursery Research in Dearing, Ga. and Griffin, Ga. in 2004 and 2006 (three reps per location, per year).

Clonally propagated plants have been evaluated in Griffin, Ga. for up to 16 years and in Blairsville, Ga. for 14 years. The first measurements were made in March 2004; half of the plants were pruned every two years to a height of 40 to 50 cm, and half were left unpruned. Height and width data were collected in Griffin every two years prior to pruning. First bloom dates were recorded each year. Winter cold and spring frost damage were assessed each spring in Griffin and Blairsville. Date of first bloom was recorded each year. Observation for disease or insect damage was continuous throughout the summer. In all evaluations, *Abelia* 'Rose Creek' (unpatented hybrid from open pollination of *Abelia chinensis* (female parent) and unknown male parent) was used as a check cultivar; the *A. chinensis* parent was also used as a check in the Griffin plots. Observations of the resulting '00-BC-46-4' progeny have shown that the unique features of this new *Abelia* '00-BC-46-4' are stable and reproduced true to type in successive generations.

*Abelia* is a genus of 15-30 species, and interspecific hybrids are popular landscape plants. They range from deciduous to evergreen, depending upon the cultivar and the climate. They have attractive, colorful foliage and flower from late spring to autumn. *Abelia* is a low-maintenance shrub that is tolerant of any well-drained soil, has heat and drought tolerance and is resistant to most pests. It thrives in full sun or part shade and can generally be grown in cold hardiness zones 5 through 9. The new *Abelia* '00-BC-46-4' plant is expected to be distributed for landscape use in the U.S. and perhaps in other countries.

SUMMARY OF THE INVENTION

The following traits have been repeatedly observed and represent the unique and distinguishing characteristics of a new variety, *Abelia* '00-BC-46-4'. The new variety '00-BC-46-4' has not been observed under all possible environmental conditions. The phenotype may vary somewhat with variations in, for example, temperature, light intensity, soil types, and water and fertility levels without, however, any variance in genotype.

Asexual reproduction of the new *Abelia* '00-BC-46-4' by softwood stem cuttings since 2004 has shown that the unique features of this new *Abelia* are stable and reproduced true to type in successive generations.

'00-BC-46-4' plants, along with 'Rose Creek' and *A. chinensis* (maternal parent of '00-BC-46-4') have been evaluated since 2001 in field plots at Griffin, Ga. and since 2006 in Blairsville, Ga. 'Rose Creek' was used as a standard for comparison as it is a popular cultivar that has *A. chinensis* as a maternal parent. Height and width data were collected in Griffin every two years on unpruned plants and prior to pruning for those pruned every two years. First bloom dates were recorded each year. Winter cold and spring frost damage was assessed each spring in Griffin and Blairsville. Date of first bloom was recorded each year. Observation for disease or insect damage was continuous throughout the summer.

Throughout this specification, color names beginning with a small letter signify that the name of that color, as used in common speech, is aptly descriptive. Color names beginning with a capital letter designate values based upon The R.H.S. Colour Chart, 2001 ($5^{th}$ edition) published by The Royal Horticultural Society, London, England.

The following traits have been consistently observed in the original plant of this new variety and in asexually propagated progeny grown from stem cuttings in Blairsville, and Griffin, Ga., and, to the best knowledge of the inventors, their combination forms the unique characteristics of the new variety '00-BC-46-4' and set it apart from all other existing varieties of *Abelia* known to the inventors.

1. '00-BC-46-4' is unique in that it has very large panicles which often become thyrsoid (FIG. 2).
2. The panicles of '00-BC-46-4 are borne on short stems (Table 1).
3. The panicles are very numerous. At peak bloom, the foliage is barely visible due to these large panicles (FIG. 1).
4. '00-BC-46-4' also has a rounded compact form (FIG. 1).

Plants of the new *Abelia* '00-BC-46-4' differ from plants of the *Abelia* cultivar 'Rose Creek' and the parental species *Abelia chinensis* in the following characteristics.

1. The new variety '00-BC-46-4' has larger compound panicles and a greater number of subpanicles than those of *A. chinensis* and 'Rose Creek'. (Table 1, FIG. 2).
2. The new variety '00-BC-46-4' has a more compact form than *A. chinensis*, with shorter internodes than *A. chinensis*. Also, the length of the stem that supports the panicle is shorter on '00-BC-46-4' than on either *A. chinensis* or 'Rose Creek' (Table 1, FIG. 1).
3. The new variety '00-BC-46-4' is shorter in height than *A. chinensis* (Table 3).
4. Sepal color of 'Rose Creek' is pink/purple, while '00-BC-46-4' and *A. chinensis* have pale green or pale pink sepals (Table 4).
5. Date of first bloom was earlier in most years for '00-BC-46-4' than for *A. chinensis* or 'Rose Creek' (Table 5).

BRIEF DESCRIPTION OF THE FIGURES

The accompanying colored photographic illustrations show the overall appearance and distinct characteristics of the new cultivar of *Abelia* '00-BC-46-4.' The colors in the photographs are as close as possible with the photographic and printing technology utilized. Colors in the photographs may differ slightly from the color values cited in the detailed botanical description, which accurately describes the colors of the new *Abelia* '00-BC-46-4'. The photographs were taken of plants grown outdoors in Georgia on the dates and locations specified below.

The photographs labeled

The photographs labeled

DETAILED BOTANICAL DESCRIPTION

Figure 1B:
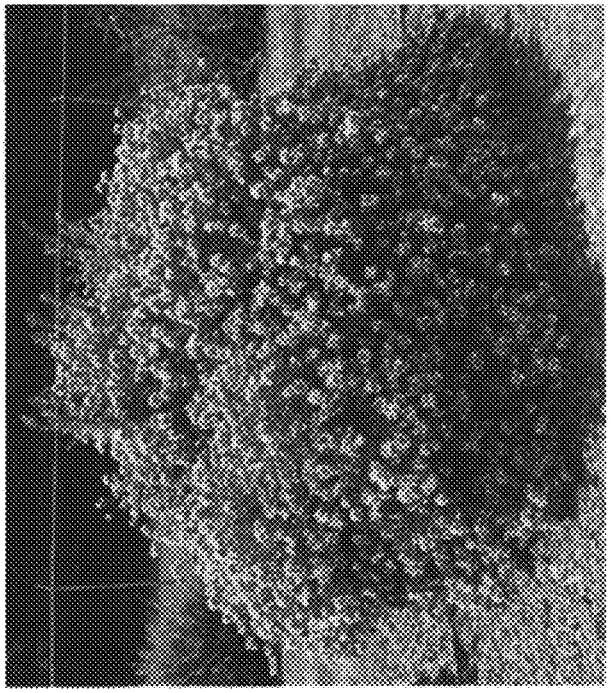
FIGS. 1A-1C depict the overall plant habit of '00-BC-46-4' (FIG. 1A, taken on Aug. 29, 2011 in Blairsville, Ga.), as compared to 'Rose Creek' (FIG. 1B taken Aug. 5, 2016 in Griffin, Ga.) and *A. chinensis* (FIG. 1C taken Aug. 23, 2004 in Griffin, Ga.).
Figure 1A:
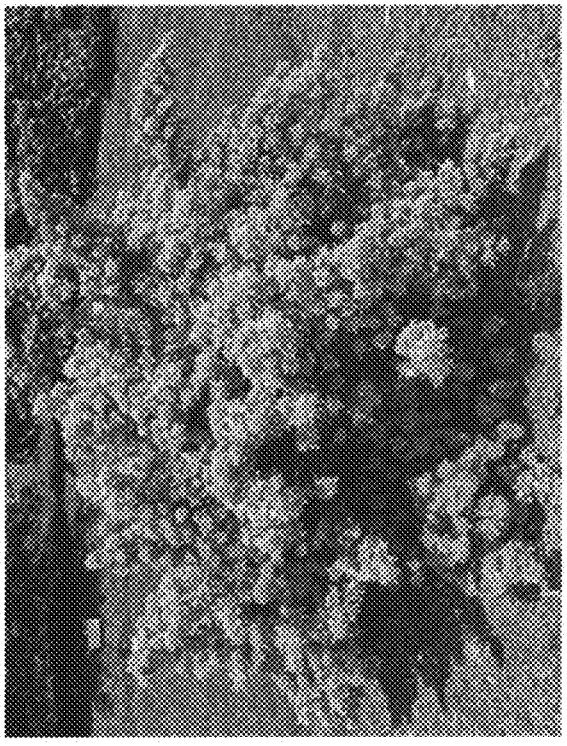
Figure 1C:
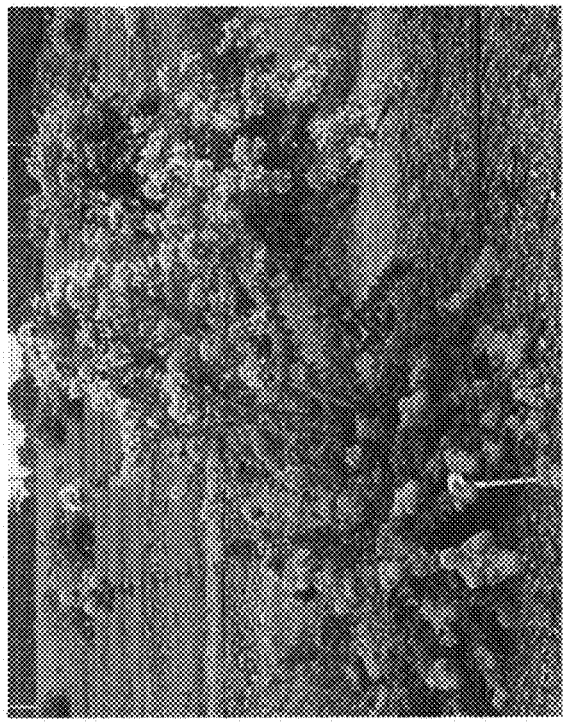
Figure 2B:
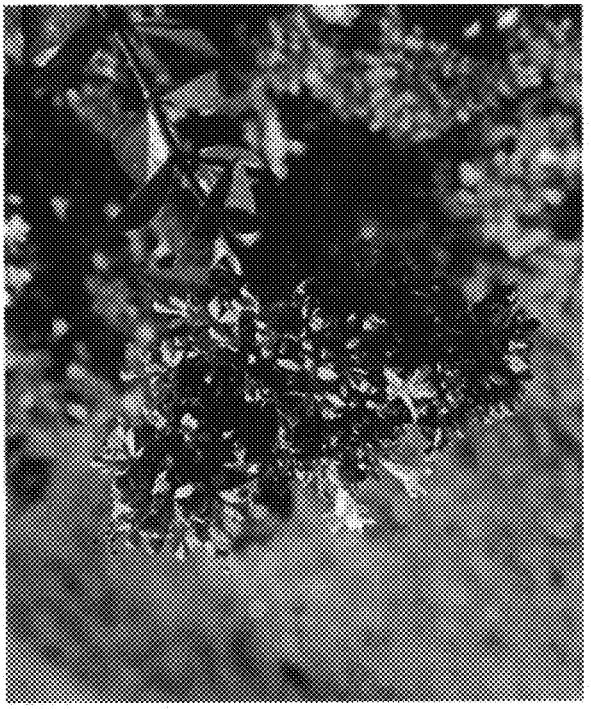
FIGS. 2A-C depict a close-up view of the compound panicles of '00-BC-46-4' (FIG. 2A taken Aug. 23, 2004 in Griffin, Ga.), as compared to 'Rose Creek' (FIG. 2B taken Aug. 8, 2019 in Griffin, Ga.) and *A. chinensis* (FIG. 2C taken Aug. 8, 2019 in Griffin, Ga.). Note sepal and flower color, as well as size.
Figure 2A:
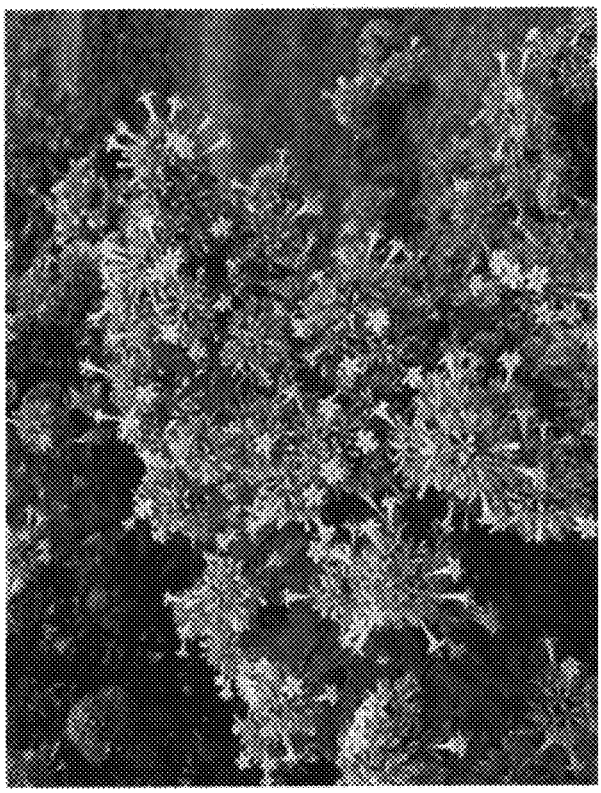
Figure 2C:
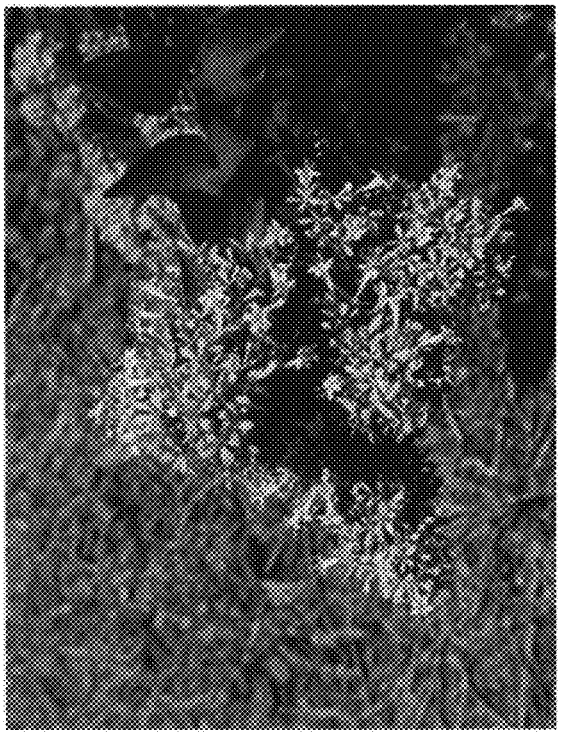

The following traits have been consistently observed in the original plant of this new variety and in asexually propagated progeny grown from stem cuttings in Blairsville, and Griffin, Ga., and, to the best knowledge of the inventors, their combination forms the unique characteristics of the new variety '00-BC-46-4'.

Throughout this specification, color names beginning with a small letter signify that the name of that color, as used in common speech, is aptly descriptive. Color names beginning with a capital letter designate values based upon The R.H.S. Colour Chart, $4^{th}$ edition published by The Royal Horticultural Society (R.H.S.), London, England in 2001.

The following observations, measurements, and values describe plants grown in Griffin, Ga. '00-BC-46-4' was propagated from softwood stem cuttings and grown in one-gallon containers prior to planting in field plots. Data are from plants planted and grown in the field since 2001, 2004 and 2006.

The new variety '00-BC-46-4' is a medium-sized *Abelia* with bright green foliage and numerous large panicles made up of white flowers with pale green sepals changing to pale pink. The large panicles of '00-BC-46-4' are especially noteworthy because they often become thyrsoid. Peak bloom occurs in mid-July, though the sepals make a stunning display through the end of summer, and the blossoms are highly fragrant. Form is upright and compact. Blooming is heavy, even on young plants in containers or in the field.

Two checks were used for comparison to '00-BC-46-4': *A. chinensis* and 'Rose Creek'. Of all available *Abelia*, the species *A. chinensis* appears most similar to '00-BC-46-4'. No commercial cultivar is similar, though 'Rose Creek' also has *A. chinensis* as a parent. Table 1 compares some morphological characteristics of the checks, 'Rose Creek' and *A. chinensis* to '00-BC-46-4'. Individual panicle size is generally larger on *A. chinensis* and much smaller on 'Rose Creek' than on '00-BC-46-4'. However, panicles typically group into compound panicles resulting in very large conical thyrse structures on '00-BC-46-4'. '00-BC-46-4' has a much more compact appearance than *A. chinensis*, as the panicles are held close to the plant rather than supported on long stems as is *A. chinensis*. The mean length of the stems supporting the panicles was 6.9 cm on '00-BC-46-4' versus 20.1 cm on *A. chinensis*. Panicles on 'Rose Creek' are intermediate in length. 'Rose Creek' has a very compact form, as is shown by the short internode length (1.2 cm), while *A. chinensis* has a very loose form (internode length 2.7 cm). '00-BC-46-4' is intermediate to the checks (2.0 cm).

Height and width data are presented in Tables 2 and 3. Half of the '00-BC-46-4' and 'Rose Creek' plants were severely pruned every two years beginning in March 2004 to a height of 40 to 50 cm. Plants were measured prior to pruning. Data shown in Table 2 were collected in 2010 and 2017 on plants that had been pruned two years earlier. Results show that in 2010, when plants had been in the field for an average of 5 years, the height of '00-BC-46-4' (86 cm) was similar in height to 'Rose Creek' (92 cm), though 'Rose Creek' was wider. However, by 2017, when the plants had been in the field for an average of 12 years, 'Rose Creek' was shorter than '00-BC-46-4'. In Table 3, height and widths are compared for plants that were field planted in 2001 and were pruned every two years. The results after 9 and 16 years of growth reveal that '00-BC-46-4' is intermediate in size to the smaller 'Rose Creek' and the larger *A. chinensis*.

Flower color of '00-BC-46-4', 'Rose Creek' and *A. chinensis* is white. However, sepal color of '00-BC-46-4' starts as green, becoming light pink, and turning brown in late summer and fall, whereas 'Rose Creek' has pink/purple sepals (Table 4). Both '00-BC-46-4' and *A. chinensis* are deciduous, while 'Rose Creek' is mostly evergreen. In Griffin, all three cultivars have their first bloom about early to mid-June (Table 5), though peak bloom is generally mid-July for '00-BC-46-4', late July for *A. chinensis*, and early August for 'Rose Creek'.

Field evaluations in Griffin since 2001 have shown very little or no cold damage on '00-BC-46-4'. Plants of '00-BC-46-4' were evaluated in Blairsville, Ga. for two winters, 2005-06 and 2006-07. Little or no cold damage was observed on '00-BC-46-4' in Blairsville, despite cold temperatures beginning in early November and continuing sporadically throughout the winter (for instance, Nov. 3, 2005 had a low temperature of −2 C, 29 F; Nov. 18, 2005 had a low temperature of −8 C, 17 F; Dec. 9, 2006 had a low temperature of −13 C, 9 F; and Jan. 29 2007 had a low temperature of −13 C, 8 F) and late spring freezes (Apr. 7, 2007 temperature of −6 C, 22 F).

Plants of the *Abelia* genus tend to drop leaves by late summer in response to heat, drought or overly wet conditions. Evaluation for leaf retention in September 2004 through 2007, following summers with heavy rainfall due to tropical depressions, or heat and drought, revealed that '00-BC-46-4' has excellent leaf retention.

'00-BC-46-4' is readily propagated through cuttings. Six-inch cuttings taken in May or early June before flowering rooted at a rate of over 70%. After 2 months, cuttings can be transferred to one-gallon containers using a well-drained potting mix. From cutting to saleable plant is about 8 months. No insect or disease problems have been noted in potted plants maintained outside the greenhouse or in field plants. Once established, the plants are quite drought resistant. After landscape establishment, a hard pruning is recommended in early spring, approximately every other year, to encourage compact growth and heavy blooming.

The aforementioned photographs and following observations, measurements, and values describe plants of the new *Abelia* '00-BC-46-4' grown in Griffin, Ga. propagated from softwood stem cuttings and grown in one-gallon containers prior to planting in field plots. Data are from plants planted and grown in the field since 2001, 2004 and 2006.

Botanical classification: *Abelia* '00-BC-46-4'.

Commercial classification: Shrub.

Parentage: Initial cross between *Abelia chinensis* (unpatented female parent) and *Abelia* x *grandiflora* (Andr) Rehd 'Francis Mason' (unpatented, male parent) produced seedling selection backcrossed to original *A. chinensis* parent, seedlings obtained from ovule culture and planted in field plot from which plant '00-BC-46-4' selected and asexually propagated.

Growth and propagation:

*Propagation type*.—By softwood stem cuttings and tissue culture.

*Growth rate*.—Softwood cuttings rooted in 5 to 6 weeks at an approximate temperature of 80° F. under the mist.

*Root description*.—White, dense, freely branched.

*Rooting habit*.—Fibrous.

Plant description:

*Form*.—Deciduous shrub, upright, compact, foliated, with heavy blooming.

*Usage*.—Various uses, such as container patio plants, potted plants, landscape uses such as border, hedge, and mass planting.

*Vigor*.—Moderate growth rate.

*Habit*.—Branches upright when young, becoming pendulous with maturity.

*Size of plant*.—Data collected on unpruned plants after 13 years growth in a field in Griffin, Ga. A. Height: 206 cm. B. Width: 305 cm.

*Stem*.—A. First Year: 1. Color: Greyed-Red 182B. 2. Diameter (at base of stem): About 1.5 mm. 3. Texture/Pubescence: Pubescent. 4. Shape: Round. 5. Odor (of bruised stem): Faint. 6. Internode Length: About 2 cm. 7. Pith: a. Type: Solid. b. Color: Yellow-Green 145D. 8. Strength: Very strong. B. Second Year: 1. Color: Brown 200C. Diameter: About 7.5 mm. Exfoliation: Developing lengthwise cracks starting about ½ way back from the tip.

*Vegetative buds*.—A. Arrangement: Opposite — some triplets. B. Type: Imbricate in opposite pairs. C. Size (length×width): Approx. ½ mm×½ mm. D. Scale Number: 6. E. Scale Color: Greyed-Purple 185B. F. Position/Disposition (angle to stem): 45°. G. Number at Node: 2-3 vegetative. H. Pubescence: Sparse, mostly along edges. I. Shape: Lanceolate.

*Leaf scar*.—A. Shape: Rounded crescent. B. Vascular Bundle Traces (number, orientation): 3 horizontal across scar. C. Pubescence: Short hairs around scar margin. D. Position of Bud (on leaf scar): Just above scar in leaf axil. E. Color Differentiation: 141D. F. Size (h×w): 1 mm×1.5 mm.

*Trunk or large stems*.—A. Color(s): Panel A between Brown 200 and Grey 201. B. What Size Stem Exfoliation Begins On: About 3.5 mm diameter. C. Diameter: About 5 mm. D. Texture: A bit rough due to striation of bark.

*Leaf*.—A. Type: Entire. B. Color Through Seasons (R.H.S.): 1. Emerging: April. a. Upper: Green 143A. b. Lower: Yellow-Green 145B. 2. Summer: July. a. Upper: Green 143A. b. Lower: Yellow-Green 145B. 3. Fall: September. a. Upper: Green 137C with Greyed-Purple. b. Lower: Yellow-Green 145B. C. Mature Size (L×W): About 3 cm×2 cm. D. Apex: Acute. E. Base: Rounded, aequilateral. F. Margin: Slightly crenate. G. Shape: Simple, rounded accuminate. H. Lobes (present/absent): Absent. I. Vein Color: Yellow-Green 147D. J. Pubescense (all surfaces): 1. Upper Surface: Scattered tiny hairs. 2. Lower Surface: Scattered tiny hairs. 3. Concentration of longer hairs along base of mid vein. 4. Single row of hairs around leaf margin. K. Arrangement on Stem: Mostly opposite, some trifoliar. L. Venation: Simple alternate. M. Texture: 1. Thickness: About 0.4 mm. 2. Degree of waxiness of surfaces: Slightly waxy. N. Odor when Crushed: Faint grassy.

*Petiole*.—A. Length: About 3 mm. B. Shape: Slightly curved and concave. C. Color (RHS): Green 137C with Greyed-Orange 176B on the edges. D. Texture/Pubescence: Sparse hairs along edges. E. Diameter: About 1 mm.

*Flower buds*.—A. Size (L×W): About 12 mm×4 mm. B. Color: Yellow-White 158A. C. Shape: Elongated teardrop. D. Pubescence: Covered in short glandular hairs. E. Time of Full Maturity: Early summer. F. Time Range for Showiness: Early summer to frost.

*Inflorescence*.—A. Type: Compound panicle sometimes becoming thyrsoid at peak bloom. B. Number per Plant: 200 to 400, depending upon the size of the mature plant. C. Size (L×W): 1. Small about 6 cm×5 cm. 2. Larger about 14 cm×10 cm. 3. Thyrse structures are much larger. D. Color: Flowers form continuously throughout the summer. 1. At emergence: White 155D. 2. Full bloom: White 155D. 3. Fading: Greyed-Yellow 161B. E. Longevity: July to frost. F. Peduncle: 1. Length: Mean 38 cm. 2. Diameter: Mean 5 mm. 3. Color (RHS): Green 143A. 4. Texture/Pubescence: Scattered short hairs. 5. Strength: Strong. 6. Aspect: 50 to 80°.

*Flower*.—A. Number per Inflorescence: 500+ at various stages of bloom. B. Axillary or Terminal: Axillary. C. Symmetry: Regular, actinomorphic. D. Size (L×W): 12 mm×8 mm. E. Fragrance: Highly floral. F. Bud: 1. Size (L×W): 12 mm×4 mm. 2. Shape: Elongated teardrop. 3. Color (RHS): Yellow-White 158A. 4. Texture/Pubescence: Covered in short glandular hairs. G. Longevity: Varies. H. Petals: 1. Number: One, gamopetalous. 2. Size (L×W): About 12 mm×8 mm. 3. Shape: Funnel, slightly tubular, gamopetalous. 4. Apex: 5 or 6 lobes, rounded and slightly curled. 5. Base: Funnel shaped with short tube approximately ⅓ the length of the flower. 6. Margin: Entire but slightly curled. 7. Color at Peak of Bloom (RHS): a. Upper Surface: White 155D. b. Lower Surface: White 155D. 8. Texture/Pubescence: Puncticulate; Outside has short glandular hairs, inside hairs are stubbier, glandular; Longer hairs extending into calyx throat. 9. Arrangement: NA. I. Pedicels: 1. Color (RHS): Green 143A. 2. Texture/Pubescence: Scattered short hairs. 3. Length: About 2 mm — bracteoles present. 4. Aspect: 45°. 5. Strength: Medium. J. Sepals: 1. Number: Mostly 5, occasionally 6. 2. Size (L×W): About 7 mm×2.5 mm. 3. Shape: Obilleptic. 4. Apex: Rounded. 5. Base: Attenuate. 6. Margin: Usually entire — rarely cleft. 7. Texture: Smooth — veinlets visible. 8. Pubescence: Covered in very short hairs. 9. Color at peak of bloom (RHS): a. Upper Surface: Yellow-Green 144C turning to Red-Purple 63D. b. Lower Surface: Yellow-Green 144D turning to Red-Purple 63C. K. Male Reproductive Structures: 1. Number: 4. 2. Anther: Dorsfixed. a. Size (L×W): About 2 mm×0.5 mm. b. Shape: Cylindrical. c. Color (RHS): White 155B. d. Texture/Pubescence: Pubescent. 3. Filament: a. Size (L×W): About 13-14 mm×0.2 mm. b. Color (RHS): White N155B. c. Texture/Pubescence: Smooth with scattered hairs. 4. Pollen: a. Quantity: Moderate. b. Color (RHS): White N155B. L. Female Reproductive Structures: 1. Pistil: a. Shape: Monostylus — Free. b. Size (L×W): About 18 mm×0.8 mm. c. Position: Epigynous — Ovary Inferior. d. Color (RHS): See stigma and style colors below. e. Pubescence: Very sparse hairs along style. 2. Stigma: a. Shape: Circular, domes. b. Color (RHS): Orange-White 159D. c. Pubescence: Puncticulate — surface made of short, clear papillose structures. 3. Style: a. Length: About 16 mm. b. Shape: Tubular. c. Color (RHS): White 155B. d. Pubescence: Very sparse hairs — mostly glabrous — surface puncticulate. 4. Ovary: a. Shape: Oval. b. Number: 1. c. Pubescence: None.

*Fruit*.—A. Type: Achene. B. Size (L×W): About 8 mm×1.5 mm. C. Color(s) During Ripening; Seeds ripen through the summer. 1. Early: Green 143C. 2. Mid: Green 143B. 3. Late: Grey-Brown N199B. D. Shape: Grooved cylindrical capsule. E. Number per Infructescence: 1. F. Pubescence: Covered in short curved hairs. G. Number of Carpels: 1. H. Persistence (effective period): Indeterminate — summer to frost.

*Seed*.—A. Shape: Achene — elongated capsule — slightly grooved longitudinally. B. Size: About 8 mm×1.5 mm. C. Color (RHS): Grey-Brown N199B. D. Number per Locule per Ovary per Fruit: 4-5 (only 1 viable embryo per seed). E. Germination Capacity: About 30%. F. Pubescence: Covered in short curved hairs.

TABLE 1

Comparison of morphological traits of '00-BC-46-4', *A. chinensis*, and 'Rose Creek'. Data were collected from field-grown plants in full sun in Griffin, Georgia.

| Cultivar | Flower size (mm) | Largest panicle Size (cm) | Mean length of stem supporting panicle (cm) |
|---|---|---|---|
| '00-BC-46-4' | 14 × 10 | 14 × 10 | 6.9 |
| *A. chinensis* | 14 × 10 | 16.5 × 12.5 | 20.1 |
| 'Rose Creek' | 12 × 11 | 5.5 × 5.5 | 11.2 |

| Cultivar | Mean Internode length (cm) | Mean length of compound panicles (cm)[1] | Mean number of subpanicles per compound panicle[1] |
|---|---|---|---|
| '00-BC-46-4' | 2.0 | 40.0 | 29.4 |
| *A. chinensis* | 2.7 | 27.0 | 14.1 |
| 'Rose Creek' | 1.2 | 11.0 | 9.2 |

[1]Length of compound panicles and number of subpanicles was determined by averaging the ten longest compound panicles on a plant of similar age.

TABLE 2

Height and width of '00-BC-46-4' and 'Rose Creek' of field-grown plants in full sun in Griffin, Georgia. Half of the plants were pruned late winter/early spring every two years beginning in March 2004 to a height of 40 to 50 cm. Prior to pruning, height and width measurements were taken. In 2010, the average age of the plants was 5 years and in 2017 the age was 12 years.

| Cultivar | Height (cm) 2010 Pruned | Width (cm) 2010 Pruned | Height (cm) 2017 Pruned | Width (cm) 2017 Pruned | Height (cm) 2017 Unpruned | Width (cm) 2017 Unpruned |
|---|---|---|---|---|---|---|
| '00-BC-46-4' | 86 | 121 | 146 | 244 | 206 | 305 |
| 'Rose Creek' | 92 | 150 | 125 | 196 | 184 | 295 |

TABLE 3

Height and width of '00-BC-46-4', 'Rose Creek' and *A. chinensis* plants field-grown in full sun in Griffin, Georgia since 2001, after 9 years (2010) and 16 years (2017) years of field growth. Plants were pruned late winter/early spring every two years beginning in March 2004 to a height of 40 to 50 cm. Prior to pruning, height and width measurements were taken.

| Cultivar | Height (cm) 2010 | Width (cm) 2010 | Height (cm) 2017 | Width (cm) 2017 |
|---|---|---|---|---|
| '00-BC-46-4' | 145 | 220 | 174 | 265 |
| 'Rose Creek' | 117 | 200 | 132 | 215 |
| *A. chinensis* | 204 | 240 | 231 | 294 |

TABLE 4

Flower and sepal color and size of '00-BC-46-4', *A. chinensis*, and 'Rose Creek'. Data were collected from field-grown plants in full sun in Griffin, Georgia on Aug. 8, 2019.

| Cultivar | Flower Color | Flower size (mm) | Sepal color | Sepal size (mm) |
|---|---|---|---|---|
| '00-BC-46-4' | White | 14 × 10 | 149C, yellow green; 181D greyed-red | 7 × 2.5 |
| *A. chinensis* | White | 14 × 10 | 149D yellow-green/182D greyed-red | 6 × 2 |
| 'Rose Creek' | White | 12 × 11 | 185D greyed-purple | 5 × 2 |

TABLE 5

Average date of first bloom of the season in 2015, 2016, and 2017 for plants grown in Griffin, Georgia. Plants were not pruned in 2015 and 2017. The number of replicates per mean is given in parentheses.

| Cultivar | 2015 Unpruned | 2016 Unpruned | 2016 Pruned | 2017 Unpruned |
|---|---|---|---|---|
| '00-BC-46-4' | June 9 (7) | June 6 (3) | June 29 (4) | May 24 (7) |
| *A. chinensis* | June 15 (1) | N/A | July 11 (1) | June 5 (1) |
| 'Rose Creek' | June 18 (8) | June 4 (3) | July 24 (5) | May 29 (8) |

What is claimed is:

1. A new and distinct cultivar of the *Abelia* plant named '00-BC-46-4' as illustrated and described herein.

* * * * *